United States Patent
Kweon et al.

(10) Patent No.: US 11,610,309 B2
(45) Date of Patent: Mar. 21, 2023

(54) METHOD AND DEVICE FOR EXTRACTING MAJOR VESSEL REGION ON BASIS OF VESSEL IMAGE

(71) Applicant: MEDIPIXEL, INC., Seoul (KR)

(72) Inventors: Jihoon Kweon, Gyeonggi-do (KR); Young-Hak Kim, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 0 days.

(21) Appl. No.: 17/834,081

(22) Filed: Jun. 7, 2022

(65) Prior Publication Data

US 2022/0301162 A1    Sep. 22, 2022

Related U.S. Application Data

(63) Continuation of application No. PCT/KR2021/001535, filed on Feb. 5, 2021.

(30) Foreign Application Priority Data

Feb. 10, 2020   (KR) .................. 10-2020-0015856

(51) Int. Cl.
| | | |
|---|---|---|
| *G06T 7/00* | (2017.01) | |
| *G06T 7/90* | (2017.01) | |
| *G06N 20/00* | (2019.01) | |
| *G06V 10/74* | (2022.01) | |

(52) U.S. Cl.
CPC ........... *G06T 7/0012* (2013.01); *G06N 20/00* (2019.01); *G06T 7/90* (2017.01); *G06V 10/761* (2022.01); *G06T 2207/20081* (2013.01); *G06T 2207/30048* (2013.01); *G06T 2207/30104* (2013.01)

(58) Field of Classification Search
CPC .................. G06T 7/0012; G06T 7/90; G06T 2207/20081; G06T 2207/30048; G06T 2207/30104; G06N 20/00; G06V 10/761
See application file for complete search history.

(56) References Cited

U.S. PATENT DOCUMENTS

| | | |
|---|---|---|
| 2018/0000441 A1 | 1/2018 | Wang et al. |
| 2019/0150869 A1 | 5/2019 | Passerini et al. |

FOREIGN PATENT DOCUMENTS

| | | |
|---|---|---|
| JP | 2015097591 A | 5/2015 |
| JP | 2017196041 A | 11/2017 |
| KR | 101697880 B1 | 1/2017 |
| KR | 1020170113251 A | 10/2017 |
| KR | 20170128975 A | 11/2017 |
| KR | 1020190115713 A | 10/2019 |

OTHER PUBLICATIONS

Machine translation for KR 2019-0115713, IDS (Year: 2019).*

(Continued)

*Primary Examiner* — Qian Yang
(74) *Attorney, Agent, or Firm* — George McGuire (57) ABSTRACT

A method for extracting a major vessel region from a vessel image by a processor may comprise the steps of: extracting an entire vessel region from a vessel image; extracting a major vessel region from the vessel image on the basis of a machine learning model which extracts a major vessel region; and revising the major vessel region by connecting separated vessel portions on the basis of the entire vessel region.

17 Claims, 7 Drawing Sheets

(56) References Cited

OTHER PUBLICATIONS

Machine translation for KR 10-1697880, IDS (Year: 2017).*
Machine translation for JP 2015-097591, IDS (Year: 2015).*
Su Yang Deep learning segmentation of major vessels in X-ray coronary angiography. Nature, Scientific Reports, <https://www.nature.com/atticles/s41598-019-53254-7>.
International Search Report and Written Opinion for PCT/KR2021/0015, dated Jun. 10, 2021. pp. 1-7.

* cited by examiner

METHOD AND DEVICE FOR EXTRACTING MAJOR VESSEL REGION ON BASIS OF VESSEL IMAGE

CROSS-REFERENCE TO RELATED APPLICATION

The present application is a by-pass continuation application under 35 U.S.C. 111(a) claiming priority to International Application number PCT/KR2021/001535, filed Feb. 5, 2021, which claims priority to Korean Patent Application No. 10-2020-0015856, filed Feb. 10, 2020, the entire disclosures of each of which are hereby incorporated by reference.

TECHNICAL FIELD

The following description relates to a device and method for extracting a major vessel region based on a blood vessel image.

BACKGROUND ART

An interventional procedure which inserts a stent using a catheter to treat a cardiac blood vessel, a cerebral blood vessel, and peripheral blood vessels is being widely spread. As a tool to set a path through which a stent passes through a guidewire or a catheter to be transported into a blood vessel, in order to transport the guidewire to an end of a diseased blood vessel, visual information based on medical images such as coronary angiography and tactile information based on fine hand sensations are utilized.

Recently, remote robots are being developed to reduce an operator's physical burden such as radiation exposure, and precisely control surgical tools. Although the surgical robots have passed FDA and are being commercialized, studies for adapting to new tools are required to perform simple procedures. Even though an operation for moving back the guidewire or rotating the guidewire at a predetermined angle is not directly performed by an operator, but is performed by the robot instead, a proportion in the operation is not so high.

DISCLOSURE OF THE INVENTION

Technical Solutions

According to an aspect, there is provided a method for extracting a major vessel region from a blood vessel image performed by a processor including extracting an entire vessel region from the blood vessel image; extracting a major vessel region from the blood vessel image based on a machine learning model which extracts a major vessel region; and correcting the major vessel region by connecting a separated portion of the blood vessel based on the entire vessel region.

According to the aspect, the machine learning model may be a machine learning model which is trained for predetermined shapes of a major blood vessel. Specifically, the machine learning model may be a machine learning model trained for a shape of at least one blood vessel of a right coronary artery (RCA), a left anterior descending artery (LAD), and a left circumflex artery (LCX).

Further, the major vessel region extracting method may further include detecting the separated portion of the blood vessel in the major vessel region. The detecting of a separated portion of the blood vessel may include: determining an area between blobs in which a shortest distance between blobs corresponding to the major vessel region is smaller than a threshold distance as the separated portion of the blood vessel.

Further, the correcting of the major vessel region may include: generating a connecting line which connects an area between blobs in which a shortest distance between blobs corresponding to the major vessel region is smaller than a threshold distance; and correcting the major vessel region by connecting the separated portion of the blood vessel in the major vessel region based on an area corresponding to the connecting line in the entire vessel region. Specifically, the correcting of the major vessel region may include: correcting the major vessel region based on an area having a shortest distance which connects the separated portion of the blood vessel, among a plurality of areas, when there is a plurality of areas which is capable of connecting the separated portion of the blood vessel corresponding to the connecting line in the entire vessel region.

The major vessel region extracting method according to the example embodiment may further include converting an RGB value of the blood vessel image into a grayscale level; and normalizing a blood vessel image which is converted into the grayscale level.

Further, the extracting of the major vessel region includes: extracting the entire vessel region based on a partial blood vessel image generated from an entire blood vessel image, and the extracting of the major vessel region may include: extracting the major vessel region based on a partial blood vessel image generated from the entire blood vessel image.

The correcting of the major vessel region according to the example embodiment may include: determining the separated portion of the blood vessel in response to a user's input to designate a position of the major vessel region; and correcting a major vessel region of a target position based on a surrounding major vessel region adjacent to the separated portion of the blood vessel.

Advantageous Effects

According to example embodiments, a major vessel region extracting method corrects a major vessel region extracted from a blood vessel image using a machine learning model to provide an image for a major vessel region without having a separated portion, thereby allowing an operator to perform accurate diagnosis and procedure.

Further, according to example embodiments, a major vessel region extracting method removes an image of micro blood vessels from a blood vessel image and separates only a vessel region of interest to be displayed as an image to allow the operator to accurately identify a blocked portion or a narrowed portion in the major blood vessel.

BEST MODE FOR CARRYING OUT THE INVENTION

Specific structural or functional descriptions for example embodiments are provided for the purpose of illustration only and may be changed in various forms to be implemented. Accordingly, example embodiments are not limited to specific disclosed forms, and the scope of the present disclosure includes changes, equivalents, or substitutions included in a technical spirit.

Even though the terms of first or second are used to describe various components, the terms should be interpreted only to distinguish one component from the other component. For example, a first component may be referred to as a second component, and similarly, a second component may be referred to as a first component.

It should be understood that, when it is described that an element is "connected" to another element, the element may be directly coupled or directly connected to the other element or coupled or connected to the other element through a third element.

A singular form may include a plural form if there is no clearly opposite meaning in the context. In the present specification, it should be understood that terms "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terminologies which are defined in a generally used dictionary should be interpreted to have the same meaning as the meaning in the context of the related art but are not interpreted as an ideally or excessively formal meaning if it is not clearly defined in this specification. Hereinafter, example embodiments will be described in detail with reference to the accompanying drawings. In each of the drawings, like reference numerals denote like elements.

Figure 1:
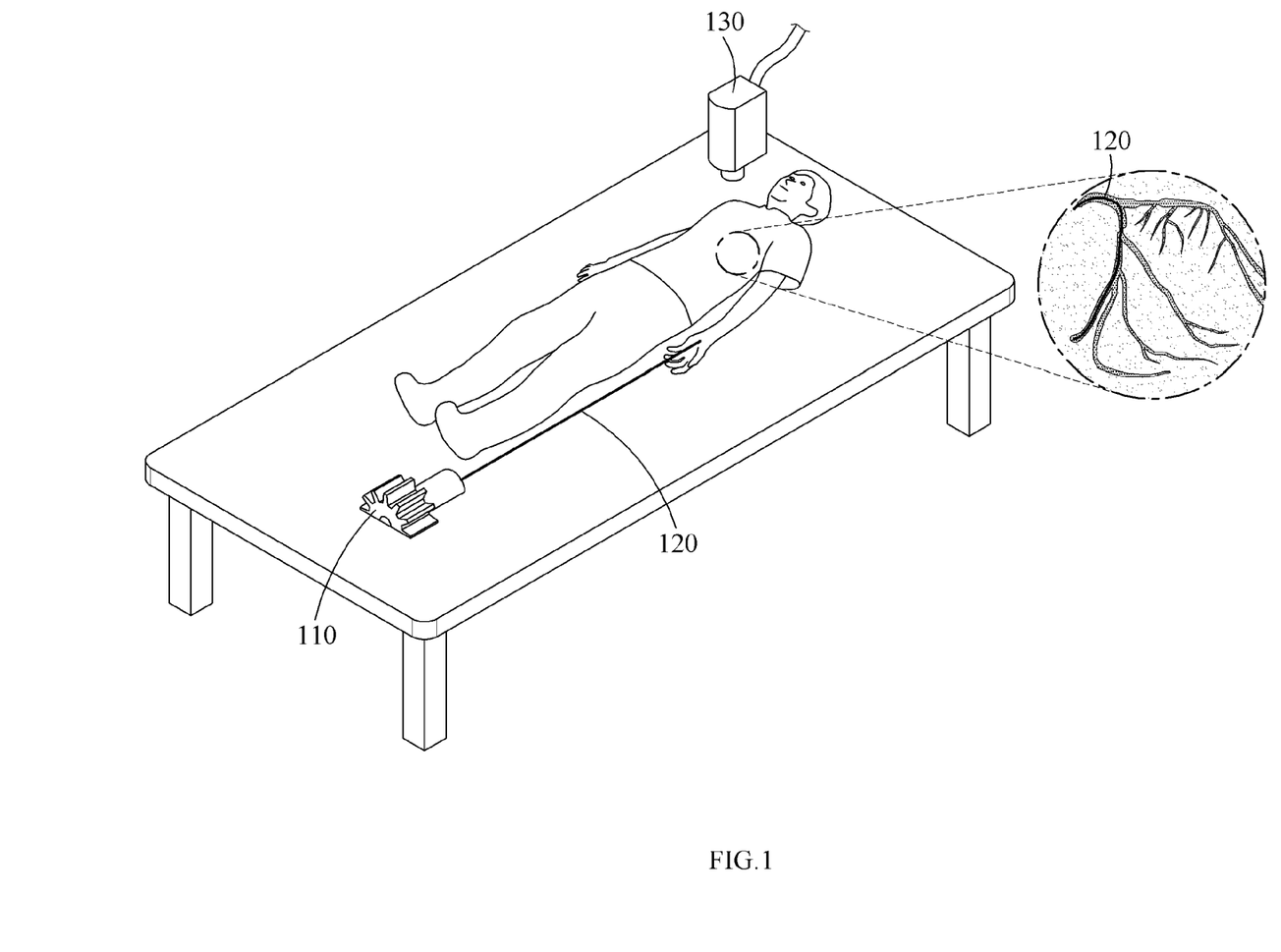
FIG. 1 is a view illustrating an operation of a medical tool inserting device and a medical tool according to an example embodiment.

FIG. 1 is a view illustrating an operation of a medical tool inserting device 110 and a medical tool 120 according to an example embodiment.

The medical tool inserting device 110 according to an example embodiment may move a medical tool 120 to a destination region of the blood vessel according to a driving command by a processor. For example, the medical tool inserting device 110 may move a tip of the medical tool 120 to a destination region of the blood vessel. The medical tool inserting device 110 may be implemented by a robot which performs a surgery and for example, a robot which controls a medical tool for cardiovascular interventional procedure.

The medical tool 120 is a member which is inserted into a blood vessel and may include a medical tool disposed at a tip of the medical tool 120 and a medical wire which connects the medical tool to a driver. For example, the medical wire includes a catheter or a guidewire. The guidewire refers to a medical wire which inserts and guides the above-mentioned medical tool to a destination part of the blood vessel. The medical tool may be a surgical tool operated in accordance with the doctor's control and for example, may be an introducer kit.

The medical tool inserting device 110 may determine the above-mentioned driving command using guide data. For example, the medical tool inserting device 110 performs an operation according to a machine learning model to output a driving command from the guide data. The machine learning model is a model which is designed and trained to receive guide data and output the guide data and for example, may be implemented by a neural network model.

The driving command may be a command which operates a driver connected to the medical tool 120 to move and rotate the medical tool 120. The driving command may be a forward command, a backward command, a clockwise rotating command, and a counterclockwise rotating command, but is not limited thereto.

The guide data refers to data in which guide information is mapped to a blood vessel image or a blood vessel structure image. The blood vessel structure image may be an image in which a specific blood vessel is extracted from the blood vessel image and the blood vessel image is preprocessed. The blood vessel structure image will be described below with reference to FIG. 3. The blood vessel image may be an image generated using coronary angiography (hereinafter, abbreviated as CAG) or a magnetic resonance imaging (hereinafter, abbreviated as MRI). In the blood vessel image, not only the blood vessel, but also the medical tool 120 may be captured.

The guide information is information for guiding movement and rotation of the medical tool 120 and for example, may include information about a starting point of the medical tool 120, a passing point, and a destination region in the blood vessel. The information about each point may include an image coordinate in a blood vessel structure image in the corresponding point, but is not limited thereto. According to the example embodiment, the guide information may be visually mapped to the blood vessel structure image. For example, a graphic object corresponding to each target region may be visualized in the blood vessel structure image and the blood vessel structure image in which the target region is visualized is referred to as a guide image.

For example, the medical tool inserting device 110 may receive guide data from an external device (for example, a guide data providing device). The guide data providing device receives and analyzes a blood vessel image from the vascular imaging device 130 and may generate guide data from the blood vessel image. As another example, the medical tool inserting device 110 may be implemented to be integrated with the above-described guide data providing device. In this case, the medical tool inserting device 110 receives a blood vessel image from the vascular imaging device 130 and analyzes the received blood vessel image to generate the guide data.

The processor of the medical tool inserting device 110 may determine the driving of the medical tool 120 based on an analysis result of the blood vessel image. The medical tool inserting device 110 analyzes the received blood vessel image to generate guide data and may determine a driving command from the generated guide data. For example, the medical tool inserting device 110 may select one of a forward command, a backward command, a clockwise rotating command, and a counterclockwise rotating command as the operation command, from the guide data. The driver of the medical tool inserting device 110 may be driven according to the selected operation command. For example, the driver may move forwardly the medical tool 120 in response to the forward command. The driver may move backwardly the medical tool 120 in response to the backward command. The driver may rotate the guidewire in a clockwise direction with respect to a longitudinal axis of the guidewire in response to the clockwise rotating command. The driver may rotate the guidewire in a counterclockwise direction with respect to a longitudinal axis of the guidewire in response to the counterclockwise rotating command.

Accordingly, the medical tool inserting device 110 determines a series of operation commands using guide data generated by analyzing the blood vessel image to move the tip of the medical tool 120 to a point guided by the guide data. The medical tool inserting device 110 repeats the determination of the operation using the guide data to move the tip of the medical tool 120 to a final destination region. After the tip of the medical tool 120, for example, after the medical tool reaches the destination region, the medical tool may perform a surgical operation in accordance to the control of a doctor. Example embodiments which will be described below with reference to FIGS. 2 to 7 relate to methods for extracting a major vessel region so that the medical tool operation device causes the medical tool to reach the destination region. However, the example embodiments are not limited thereto and the example embodiments may be a method for extracting a major vessel region to allow an operator to determine which vessel region is required to be subject to the procedure from the major blood vessel.

Figure 2:
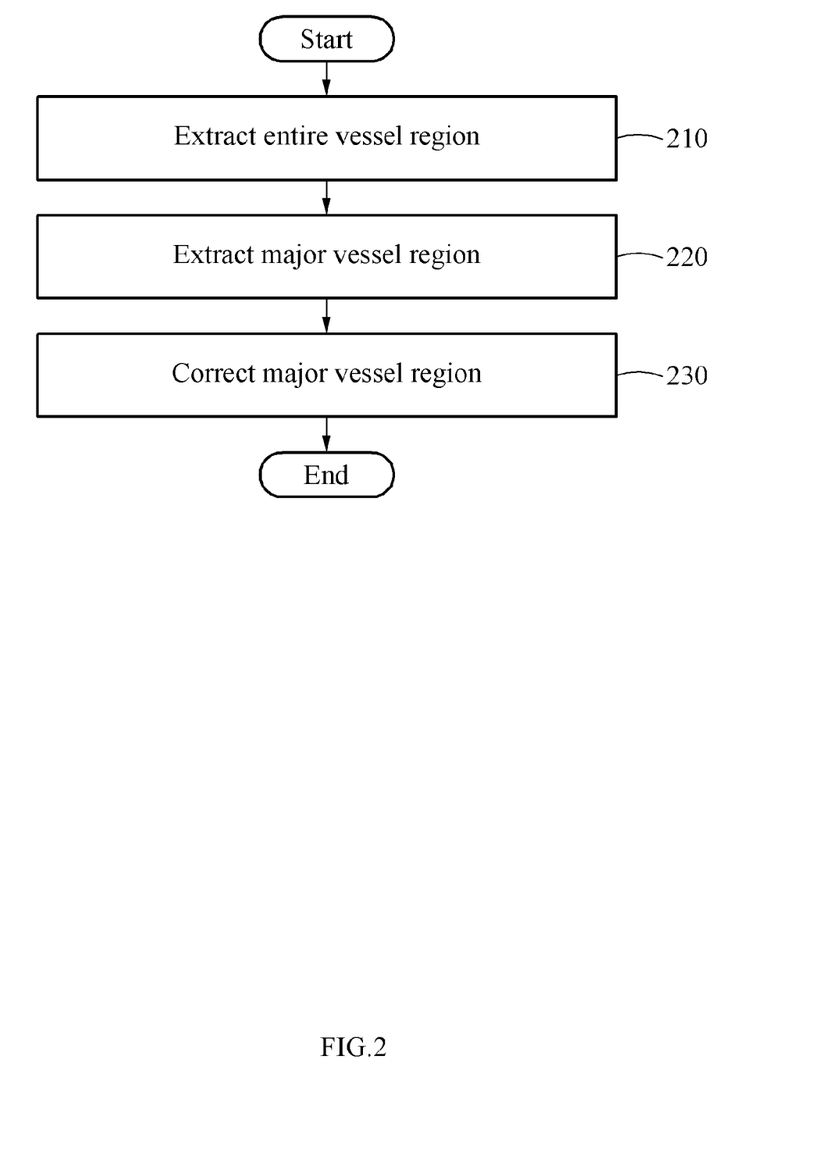
FIG. 2 is a flowchart illustrating a method for extracting and correcting a major vessel region from a blood vessel image according to an example embodiment.

FIG. 2 is a flowchart illustrating a method for extracting and correcting a major vessel region from a blood vessel image according to an example embodiment.

In step 210, a processor configured to extract a major vessel region may extract an entire vessel region from the blood vessel image. The processor according to the example embodiment may extract the entire vessel region based on a machine learning model which extracts an entire vessel region. The machine learning model which extracts the entire vessel region may be a model trained using Python (Anaconda version 2.7.14). A deep learning library used for training the machine learning model may use Theano backend of Keras, but is not necessarily limited thereto and also use TensorFlow or PyTorch, and the machine learning model may use U-net. U-net is a model developed for patch based biomedical image segmentation and may show an acceptable performance with a small number of data.

According to another example embodiment, the processor may extract the entire vessel region by detecting a boundary based on a grayscale level difference between pixels and neighboring pixels in the blood vessel image. For example, the processor may detect an area in which the grayscale level of an arbitrary pixel and a neighboring pixel is sharply changed as a boundary or detect a pixel in which a gradient value of the grayscale level is larger than a threshold gradient value as a boundary.

In step 220, the processor may extract a major vessel region from a blood vessel image based on a machine learning model which extracts a major vessel region. The machine learning model which extracts the major vessel region may be a machine learning model trained for predetermined shapes of the major vessels. For example, the major vessels may be three cardiac blood vessels including one right coronary artery and two left coronary arteries. At this time, the machine learning model may be trained for at least one vascular shape of one right coronary artery and two left coronary arteries.

For example, the processor may extract a major vessel region based on the machine learning model which is trained for the shapes of three major blood vessels. Python (anaconda version 3.5.2) may be used for the training the major blood vessels. The deep learning library used for training the major blood vessel is TensorFlow (1.4.0).

The processor may use PSPNET as a machine learning model to extract the major vessel region. PSPNET is useful to learn a context on the entire image and is excellent to simultaneously segment a plurality of layers. In addition to PSPNET, any of deep learning models which use the entire image size as an input may be used.

As data used for the learning, a 512×512 image is used, but when the learning is performed in the model, the image is resized to 720×720 to be used.

In step 230, the processor connects a separated portion of the blood vessel based on the entire vessel region to correct the major vessel region. The correction of the extracted major vessel region will be described below with reference to FIGS. 5 and 6.

Figure 3:
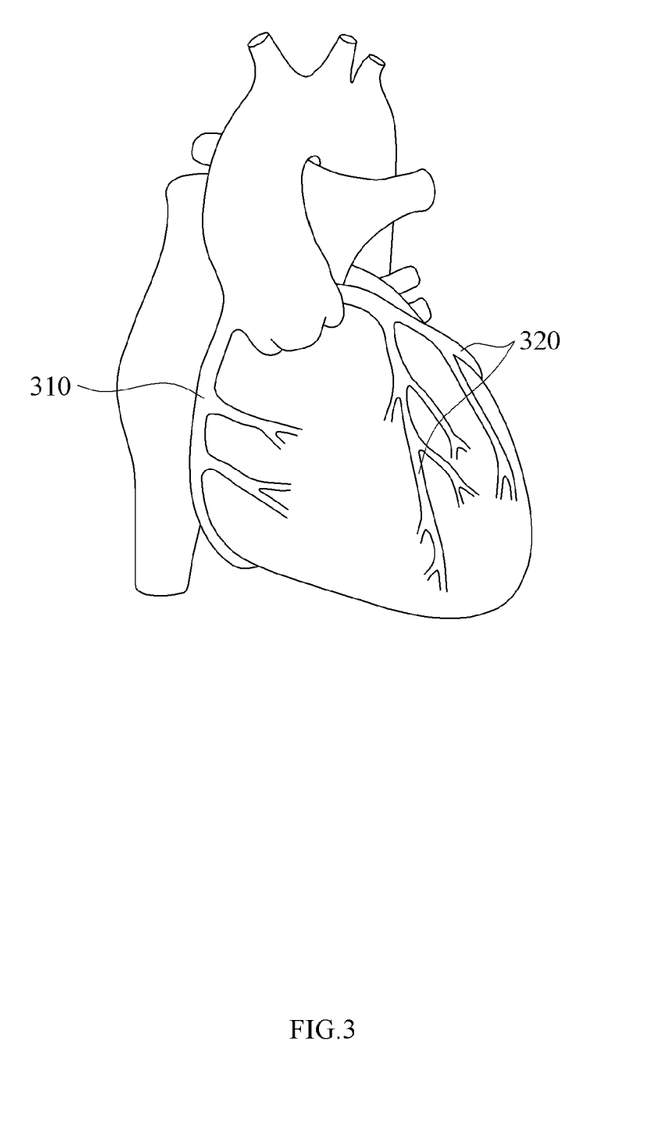
FIG. 3 is a view illustrating a cardiac blood vessel to be extracted as a major vessel region according to an example embodiment.

FIG. 3 is a view illustrating a cardiac blood vessel to be extracted as a major vessel region according to an example embodiment.

The major blood vessel according to the example embodiment may be a cardiac blood vessel, and FIG. 3 illustrates an aorta which supplies blood to the heart and three coronary arteries receiving the blood from the aorta, that is, one right coronary artery 310 and two left coronary arteries 320. The right coronary artery 310 and the left coronary arteries 320 supply blood to a large number of micro blood vessels.

Since the number of micro blood vessels is large, even though one or two micro blood vessels are narrowed or blocked, there is no problem to supply blood in most cases. Accordingly, the operator's diagnosis is usually focused on determining whether there is a blockage or narrowing of the right coronary artery 310 and the left coronary arteries 320.

However, since there are numerous micro blood vessels around the coronary arteries, it is difficult for even an experienced operator to separate the coronary arteries from the micro blood vessels to determine whether the blood vessels are narrowed or blocked.

Accordingly, the processor according to the example embodiment may extract a right coronary artery and the left coronary artery which are major vessel regions, based on the machine learning model trained for the shapes of the right coronary artery and the left coronary artery. Therefore, the operator may determine whether the procedure for the major blood vessels is required based on the major vessel region generated by the processor.

Figure 4:
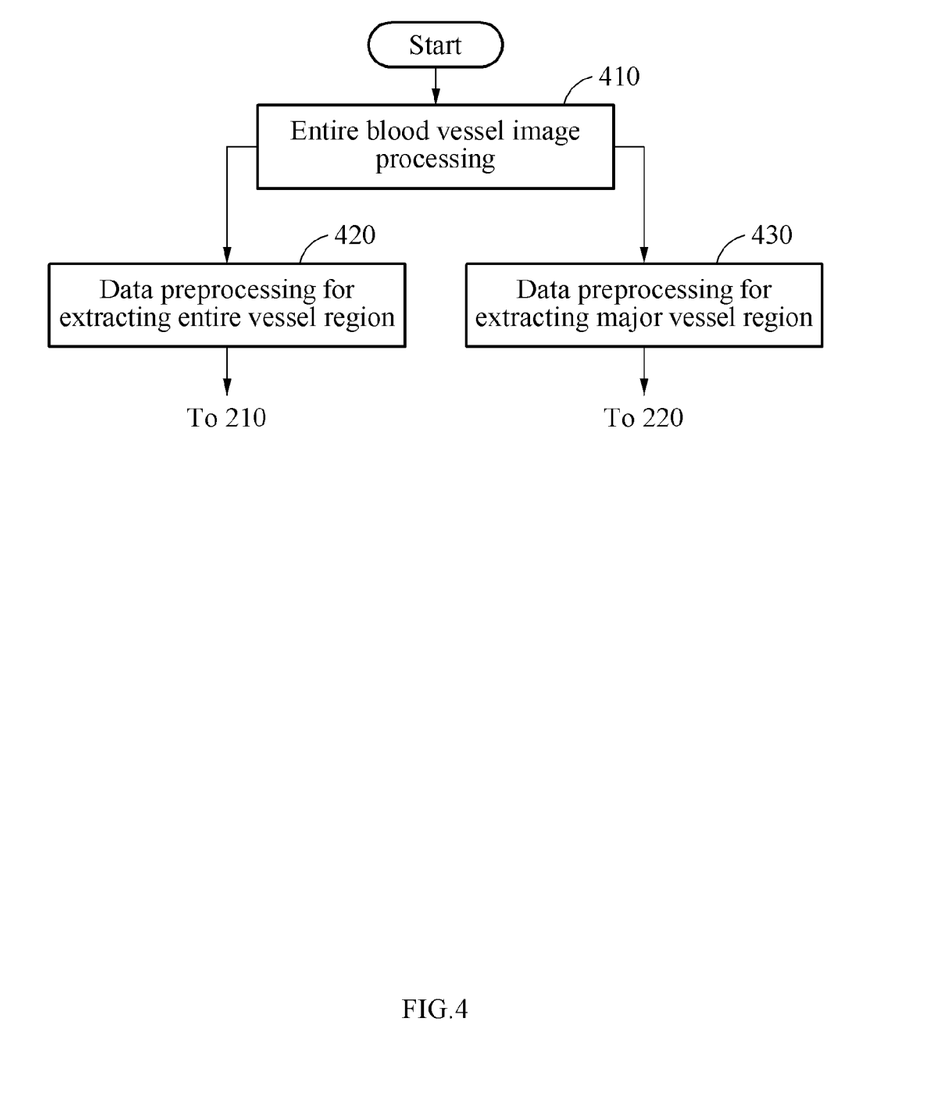
FIG. 4 is a flowchart illustrating a preprocessing method for extracting a major vessel region and an entire vessel region according to an example embodiment.

FIG. 4 is a flowchart illustrating a preprocessing method for extracting a major vessel region and an entire vessel region according to an example embodiment.

The processor according to an example embodiment may preprocess the entire vessel image after receiving a blood vessel image from the image capturing device in step 410. As a blood vessel image format to be processed an image, a 512×512 image in a bmp format extracted in a digital imaging and communications in medicine (DICOM) format may be as a default, but is not necessarily limited thereto. That is, the image size may be large enough to distinguish the blood vessels and the format of the image may use various formats such as portable network graphic (png) format, as well as the bitmap (bmp) format. The processor crops all edges of both the image and the mask file by 20 pixels to remove the noise of the surrounding portions.

In step 420, the processor may preprocess the blood vessel image to extract the entire vessel region. The processor according to the example embodiment may generate a partial blood vessel image from the entire blood vessel image. At this time, the partial blood vessel image may use a bmp format. However, the format of the partial blood vessel image is not limited thereto and the size of the image may be large enough to distinguish the blood vessel and the format of the image may use various formats other than the bmp format.

The processor converts a RGB value of the partial blood vessel image into a gray scale value using an in-house program and normalizes the gray scale image obtained as a result.

The partial blood vessel image of the entire vessel region may be formed such that an area which is not masked as a black and white image has 0 and a masked area has a value of 255 and the image is used to be resized to 256×256.

The processor may extract the entire vessel region in step 210 from the image which has been completed to be preprocessed in step 420.

In step 430, the processor may preprocess the blood vessel image to extract the major vessel region. The processor according to the example embodiment may generate a partial blood vessel image from the entire blood vessel image. At this time, the blood vessel image and the mask of the partial blood vessel image may use a png format, but is not necessarily limited thereto. The mask png file may be formed such that an area which is not masked has 0 and a masked area has 1. Further, the image may be used to be resized to 512×512. The processor may extract the major vessel region in step 220 from the image which has been completed to be preprocessed in step 430.

Figure 5:
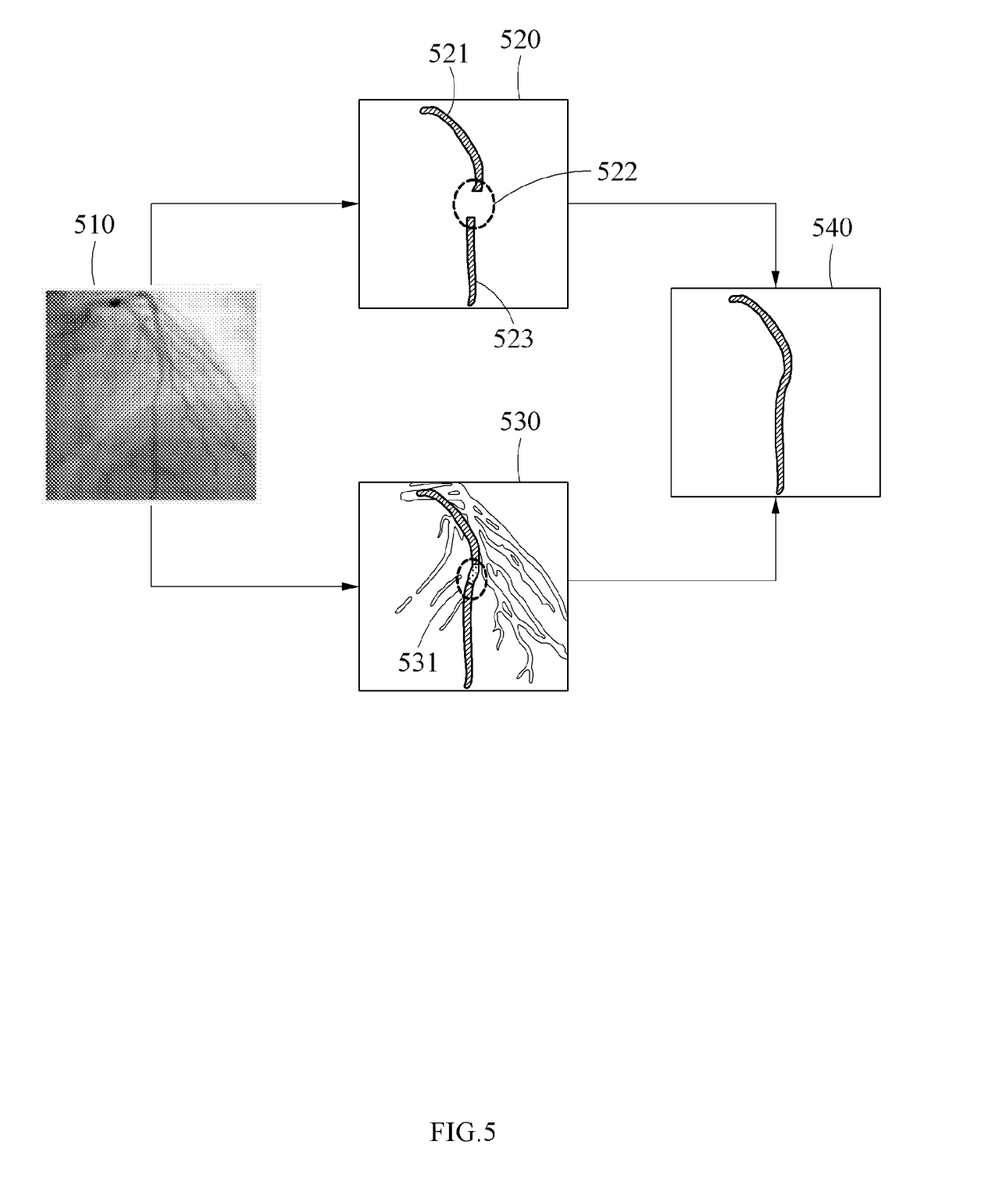
FIG. 5 is a view illustrating that a major vessel region is corrected based on an entire vessel region according to an example embodiment.

FIG. 5 is a view illustrating that a major vessel region is corrected based on an entire vessel region according to an example embodiment.

The processor according to the example embodiment may extract a major vessel region 520 and an entire vessel region 530 from the blood vessel image 510. When the processor extracts the major vessel region 520 based on the machine learning model, even though the blood vessel is connected actually, there may be a portion 522 in which the blood vessel is separated. The entire vessel region 530 includes a major vessel region so that the processor may correct the major vessel region 520 by connecting the separated portion 522 of the blood vessel in the major vessel region 520, based on the entire vessel region 530.

The processor may detect the separated portion 522 of the blood vessel in the major vessel region 520. According to the example embodiment, an area between the blobs 521 and 523 in which a shortest distance between the blobs corresponding to the major vessel region 520 is shorter than a threshold distance may be determined as the separated portion 522 of the blood vessel. The blob (binary large object) is a chunk having a predetermined size or larger in an image (for example, a binary image) and may be a group in which a number of pixels which is equal to or more than a threshold ratio to the image size are connected. For example, pixels indicating the blood vessel region may be extracted from the blood vessel image 510 and objects indicated by a group in which a number of pixels which is equal to or more than a threshold ratio is connected, among the extracted pixels, may be blobs 521 and 523 illustrated in FIG. 5. For example, the processor measures the size of the blobs 521 and 523 in the unit of the number of pixels and objects in which the number of connected pixels is 10% or more of the image size, among the objects, may be set as blobs 521 and 523 corresponding to at least a part of the major blood vessel. When a size of a portion represented as the major vessel region 520 is smaller than a predetermined size, the processor may classify the object which is smaller than a predetermined size as a noise. The processor may exclude the object classified as a noise from the major vessel region 520.

After determining objects having a predetermined size or larger, in the major vessel region 520, as blobs 521 and 523, the processor compares the shortest distance between the blobs 521 and 523 and a threshold distance to determine whether the area between the blobs 521 and 521 corresponding to the major vessel region 520 is a separated portion 522 of the blood vessel. For example, when the shortest distance between the blobs 521 and 523 is short, even though the blobs 521 and 523 are actually connected, the blobs may be captured and extracted as if the blobs are separated, due to the noise. At this time, the processor according to the example embodiment may determine that the blobs 521 and 523 correspond to the same blood vessel in response to the case when the shortest distance between the blobs 521 and 523 is shorter than a threshold ratio distance of the image size.

The processor according to the example embodiment may generate a connecting line to connect the blobs 521 and 523 in an area between the separated blobs 521 and 523 in response to the case when the shortest distance between the blobs 521 and 523 corresponding to the major vessel region 520 is shorter than a threshold ratio distance. The connecting line refers to a line which connects the separated blobs 521 and 523 in the major vessel region 520.

The processor may match an image size of the entire vessel region 530 to an image size of the major vessel region 520 to correct the major vessel region 520 based on the entire vessel region 530. For example, the image size of the entire vessel region 530 is 256×256 pixels and the image size of the major vessel region 520 is 768×768 pixels, which are different from each other. The processor scales at least one of the image size of the entire vessel region 530 and the image size of the major vessel region 520 to match image sizes of two regions.

After matching the image sizes, the processor may connect the separated portion 522 of the blood vessel in the major vessel region 520 based on the region corresponding to the connecting line of the entire vessel region 530 to output the corrected major vessel region 540. The processor may determine a region 531 corresponding to the connecting line of the major vessel region 520 from the entire vessel region 530. For example, the processor may determine the region 531 corresponding to a pixel position indicated by the connecting line of the major vessel region 520 from the entire vessel region 530. The processor may connect the separated portion 522 of the blood vessel by applying the determined region 531 to the major vessel region 520. For example, the processor performs a region growing on the separated portion 522 between the blobs 521 and 523 based on the determined region 531 to connect the blobs 521 and 523.

When there is a plurality of regions which connects the separated portion 522 of the blood vessel corresponding to the connecting line, in the entire vessel region 530, the processor may correct the major vessel region 520 based on a region having the shortest distance which may connect the separated portion 522 of the blood vessel, among the plurality of regions.

The processor according to the example embodiment may compare thicknesses of the corresponding blood vessels in the entire vessel region 530 and the major vessel region 520 and enlarge the major vessel region 520 which is extracted to be thinner than an actual thickness of the blood vessel, based on the entire vessel region 530 to correct the major vessel region 520. For example, in an arbitrary point of the blood vessel, when a vessel thickness of the major vessel region 520 is a first thickness and a vessel thickness of the entire vessel region 530 is a second thickness which is larger than the first thickness, the processor may enlarge the vessel thickness of the major vessel region 520 from the first thickness to the second thickness. Accordingly, the processor corrects the major vessel region 520 which is output to be thin or be separated, from the machine learning model which extracts the major vessel region, to precisely extract a vessel region which is not extracted by the machine learning model.

Figure 6:
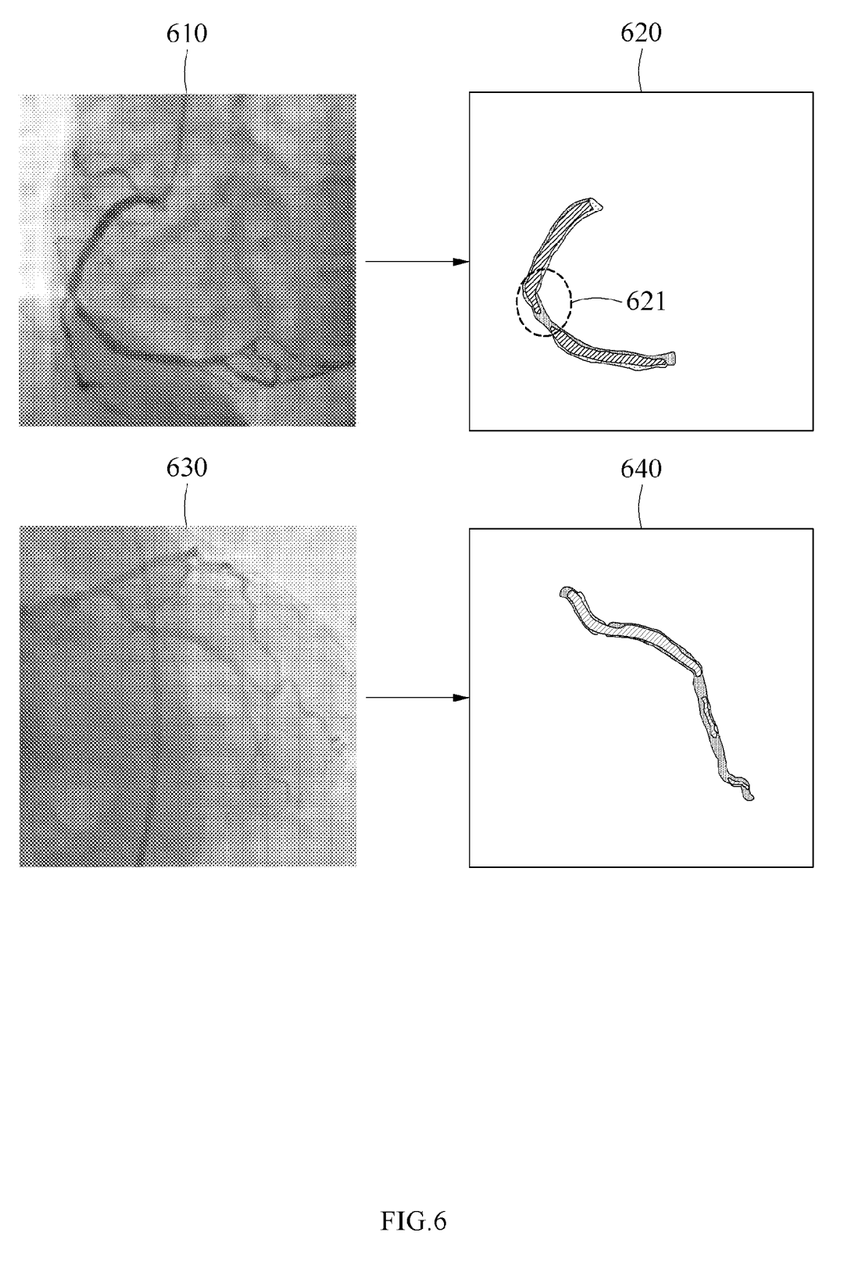
FIG. 6 is a view illustrating that a corrected major vessel region is extracted from a blood vessel image according to an example embodiment.

FIG. 6 illustrates that corrected major vessel regions 620 and 640 are extracted from blood vessel images 610 and 630, according to an example embodiment.

In FIG. 6, when images are only generated by a machine learning model which extracts major vessel regions 620 and 640 with respect to blood vessel images 610 and 630 displayed on a left cardiovascular X-ray image, but are not corrected based on the entire vessel region, even though a part of the actual major blood vessel is narrowed, the processor recognizes the narrowed part as a noise such as micro blood vessels to remove. However, the narrowed portion is a part of the major blood vessel and the narrowed state expresses the current situation as the best way, so that when the narrowed portion is removed, correct diagnosis may be disrupted.

In contrast, the entire vessel region image is an image generated for the entire blood vessel regardless of a size of the vessel width, so that even though a part of the major blood vessel is narrowed, the processor does not determine the narrowed part as a noise to remove the narrowed part but outputs it as it is.

Accordingly, the processor extracts the major vessel regions 620 and 640 for the blood vessel images 610 and 630 and then displays a part recognized by the entire vessel region instead of a separated portion 621 of the blood vessel so that only the major blood vessel among the blood vessels displayed in the blood vessel images 610 and 630 is accurately extracted to be displayed on a screen.

Further, in this case, the processor displays a blood vessel portion which replaces the extracted separated portion of the blood vessel in the major vessel regions 620 and 640 with different colors to emphasize that the corresponding portion of the major blood vessel is a narrowed portion to the operator.

Further, the processor combines an image obtained from the major vessel regions 620 and 640 and an image obtained from the entire vessel region to output a result image so that information concerning how much the narrowed portion is narrowed from a size and a thickness of the major blood vessel may be provided to the operator. The major vessel region extracting apparatus may calculate and output a ratio of the thickness of the narrowed portion of the blood vessel with respect to the thickness of the major blood vessel as a level of stenosis. For example, the processor compares the entire vessel region and the major vessel regions 620 and 640 to calculate how many percentages the narrowed portion is narrowed compared with the thickness of the major blood vessel to display the percentage on the screen.

Furthermore, the processor compares the entire vessel region and the major vessel regions 620 and 640 to each other and suggests a most appropriate treatment for a patient on the screen. For example, the processor may display one of the following information on the screen.

"No specific action required"
"Medication is required"
"Coronary angioplasty is required"

According to the present disclosure as described above, the processor removes an image of the micro blood vessels from the major blood vessel images 610 and 630 obtained by the angiography and separates only the major blood vessels of interest to be displayed as images so that the operator may more accurately find out a blocked portion or a narrowed portion of the major blood vessel and more accurately diagnose.

The major vessel region extracting apparatus according to the example embodiment utilizes the artificial intelligence technique to separate only the major blood vessels and display the major blood vessels as images to increase a separation degree of the major blood vessels. Further, the major vessel region extracting apparatus utilizes the artificial intelligence technique to separately display blood vessels included in the blood vessel images 610 and 630 to be distinguished from elements other than the blood vessels, that is, another elements such as a plastic tube for injecting a contrast media or organs so that the operator may more accurately find out a blocked or narrowed portion of the major blood vessel. Moreover, when the major vessel region extracting apparatus utilizes the artificial intelligence technique, the processor separates and displays the blood vessels included in the blood vessel images 610 and 630 for the major blood vessel and separates and displays the blood vessels for the entire blood vessel through different routes and combines the learning data acquired as a result to improve the extraction accuracy as compared by the extraction of only the major blood vessel by the learning. Further, the major vessel region extracting apparatus displays a blockage or narrowing degree of the major blood vessel as a numerical value based on the output obtained as described above to allow more objective judgement.

Figure 7:
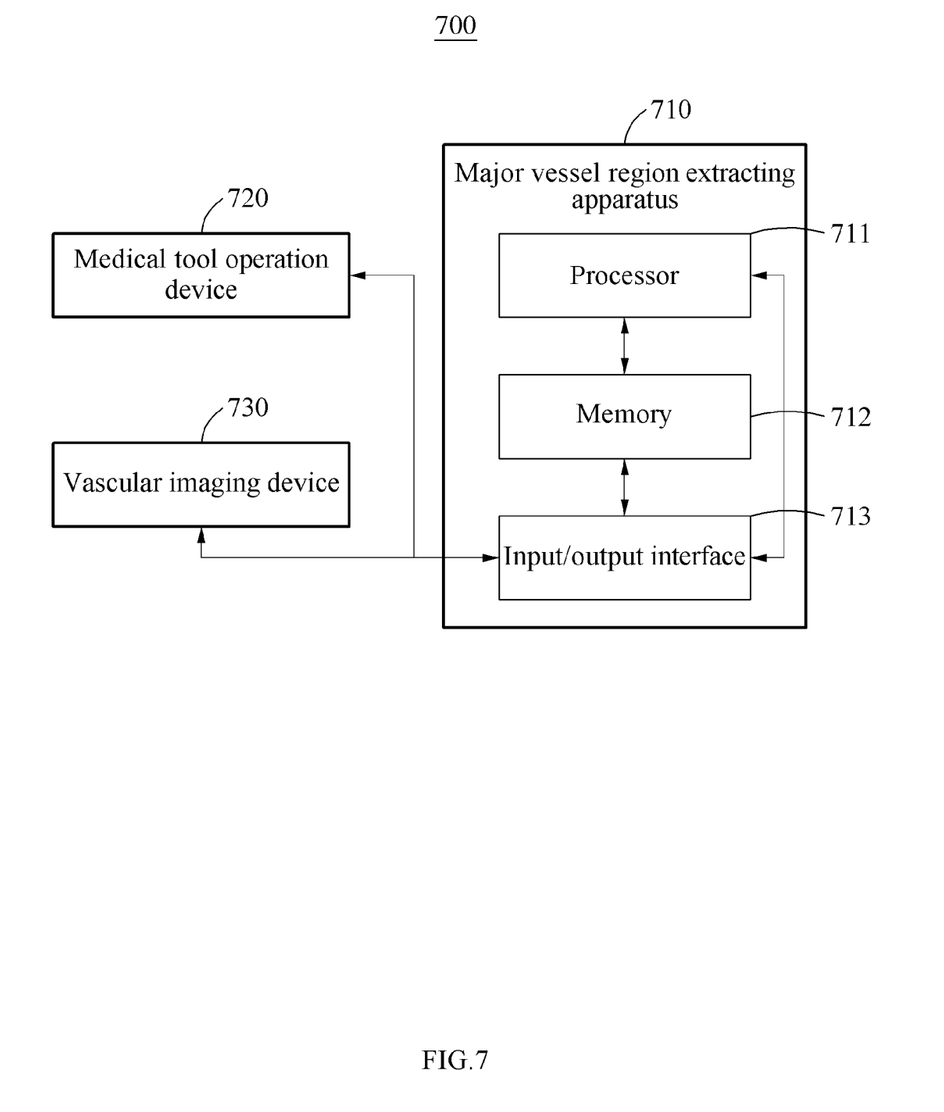
FIG. 7 is a block diagram illustrating a schematic configuration of an apparatus for extracting a major vessel region according to an example embodiment.

FIG. 7 is a block diagram illustrating a schematic configuration of an apparatus for extracting a major vessel region according to an example embodiment.

A system 700 for extracting a major vessel region according to an example embodiment may include at least one of a major vessel region extracting apparatus 710, a medical tool operation device 720, and a vascular imaging device 730. The major vessel region extracting apparatus 710 may include a processor 711, a memory 712, and an input/output interface 713.

The processor 711 extracts an entire vessel region from a blood vessel image, extracts a major vessel region from the blood vessel image based on a machine learning model which extracts the major vessel region, and connects a separated portion of the blood vessel based on the entire vessel region to correct the major vessel region. The process performed by the processor 711 to extract and correct the major vessel region has been described above with reference to FIGS. 2 to 6, so that a detailed description will be omitted. The memory 712 temporally stores at least one of a blood vessel image, an entire vessel region, a major vessel region, and a machine learning model and the processor 711 loads the data stored in the memory 712 to extract and correct the major vessel region. The input/output interface 713 is connected to at least one of the vascular imaging device 730 and the medical tool operation device 720 to transmit and receive data.

The example embodiments described above may be implemented by a hardware component, a software component, and/or a combination of the hardware component and the software component. For example, the device, the method, and the components described in the example embodiments may be implemented, for example, using one or more general purpose computers or special purpose computers such as a processor, a controller, an arithmetic logic unit (ALU), a digital signal processor, a microcomputer, a field programmable gate array (FPGA), a programmable logic unit (PLU), a microprocessor, or any other device which executes or responds instructions. The processing device may perform an operating system (OS) and one or more software applications which are performed on the operating system. Further, the processing device may access, store, manipulate, process, and generate data in response to the execution of the software. For ease of understanding, it may be described that a single processing device is used, but those skilled in the art may understand that the processing device may include a plurality of processing elements and/or a plurality of types of processing element. For example, the processing device may include a plurality of processors or include one processor and one controller. Further, another processing configuration such as a parallel processor may be allowed.

The software may include a computer program, a code, an instruction, or a combination of one or more of them and configure the processing device to be operated as desired or independently or collectively command the processing device. The software and/or data may be permanently or temporarily embodied in an arbitrary type of machine, component, physical device, virtual equipment, computer storage medium or device, or signal wave to be transmitted to be interpreted by a processing device or provide command or data to the processing device. The software may be distributed on a computer system connected through a network to be stored or executed in a distributed manner. The software and data may be stored in one or more computer readable recording media.

The method according to the example embodiment may be implemented as a program command which may be executed by various computers to be recorded in a computer readable medium. The computer readable medium may include solely a program command, a data file, a data structure, and the like, or a combination thereof. The program instruction recorded in the medium may be specifically designed or constructed for the example embodiment or known to those skilled in the art of a computer software to be used. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high level language code which may be executed by a computer using an interpreter. The hardware device may operate as one or more software modules in order to perform the operation of the example embodiment and vice versa.

As described above, although example embodiments have been described by limited drawings, those skilled in the art may apply various technical modifications and changes based on the above description. For example, even when the above-described techniques are performed by different order from the described method and/or components such as systems, structures, devices, or circuits described above are coupled or combined in a different manner from the described method or replaced or substituted with other components or equivalents, the appropriate results can be achieved.

The invention claimed is:

1. A method for extracting a major vessel region from a blood vessel image performed by a processor, the method comprising:
   extracting an entire vessel region from the blood vessel image;
   extracting a major vessel region from the blood vessel image based on a machine learning model which extracts a major vessel region;
   detecting the separated portion of the blood vessel in the major vessel region; and
   correcting the major vessel region by connecting a separated portion of the blood vessel based on the entire vessel region,
   wherein the detecting of the separated portion of the blood vessel includes:
   determining an area between blobs in which a shortest distance between blobs corresponding to the major vessel region is smaller than a threshold distance as the separated portion of the blood vessel.

2. The major vessel region extracting method of claim 1, wherein the machine learning model is a machine learning model which is trained for predetermined shapes of a major blood vessel.

3. The major vessel region extracting method of claim 2, wherein the machine learning model is a machine learning model trained for a shape of at least one blood vessel of a right coronary artery (RCA), a left anterior descending artery (LAD), and a left circumflex artery (LCX).

4. The major vessel region extracting method of claim 1, wherein the correcting of the major vessel region includes:
   generating a connecting line which connects an area between blobs in which a shortest distance between blobs corresponding to the major vessel region is smaller than a threshold distance; and
   correcting the major vessel region by connecting the separated portion of the blood vessel in the major vessel region based on an area corresponding to the connecting line in the entire vessel region.

5. The major vessel region extracting method of claim 4, wherein the correcting of the major vessel region includes:
   correcting the major vessel region based on an area having a shortest distance which connects the separated portion of the blood vessel, among a plurality of areas, when there is the plurality of areas which is capable of connecting the separated portion of the blood vessel corresponding to the connecting line in the entire vessel region.

6. The major vessel region extracting method of claim 1, further comprising:
   converting an RGB value of the blood vessel image into a grayscale level; and
   normalizing a blood vessel image which is converted into the grayscale level.

7. The major vessel region extracting method of claim 1, wherein the extracting of the entire vessel region includes:
   extracting the entire vessel region based on a partial blood vessel image generated from an entire blood vessel image, and the extracting of the major vessel region includes:
extracting the major vessel region based on a partial blood vessel image generated from the entire blood vessel image.

8. The major vessel region extracting method of claim 1, wherein the correcting of the major vessel region includes:
determining the separated portion of the blood vessel in response to a user's input to designate a position of the major vessel region; and
correcting a major vessel region of a target position based on a surrounding major vessel region adjacent to the separated portion of the blood vessel.

9. A non-transitory computer-readable storage medium storing instructions that, when executed by one or more processors, configure the one or more processors to perform the method of claim 1.

10. A major vessel region extracting apparatus, comprising:
a processor configured to extract an entire vessel region from a blood vessel image, extract a major vessel region from the blood vessel image based on a machine learning model which extracts a major vessel region, detect the separated portion of the blood vessel in the major vessel region, and correct the major vessel region by connecting a separated portion of the blood vessel based on the entire vessel region; and
a memory configured to store at least one of the blood vessel image, the entire vessel region, the major vessel region, and the machine learning model,
wherein the processor determines an area between blobs in which a shortest distance between blobs corresponding to the major vessel region is smaller than a threshold distance as the separated portion of the blood vessel.

11. The major vessel region extracting apparatus of claim 10, wherein the machine learning model is a machine learning model which is trained for predetermined shapes of a major blood vessel.

12. The major vessel region extracting apparatus of claim 11, wherein the machine learning model is a machine learning model trained for a shape of at least one blood vessel of a right coronary artery (RCA), a left anterior descending artery (LAD), and a left circumflex artery (LCX).

13. The major vessel region extracting apparatus of claim 10, wherein the processor generates a connecting line which connects an area between blobs in which a shortest distance between blobs corresponding to the major vessel region is smaller than a threshold distance and corrects the major vessel region by connecting the separated portion of the blood vessel in the major vessel region based on an area corresponding to the connecting line in the entire vessel region.

14. The major vessel region extracting apparatus of claim 13, wherein when there is a plurality of areas which is capable of connecting the separated portion of the blood vessel corresponding to the connecting line in the entire vessel region, the processor corrects the major vessel region based on an area having a shortest distance which connects the separated portion of the blood vessel, among the plurality of areas.

15. The major vessel region extracting apparatus of claim 10, wherein the processor converts an RGB value of the blood vessel image into a grayscale level and normalizes a blood vessel image which is converted into the grayscale level.

16. The major vessel region extracting apparatus of claim 10, wherein the processor extracts the entire vessel region and the major vessel region based on a partial blood vessel image generated from the entire blood vessel image.

17. The major vessel region extracting apparatus of claim 10, wherein the processor determines the separated portion of the blood vessel in response to a user's input to designate a position of the major vessel region and corrects a major vessel region of a target position based on a surrounding major vessel region adjacent to the separated portion of the blood vessel.

* * * * *